United States Patent [19]

Yam

[11] Patent Number: 5,215,977

[45] Date of Patent: Jun. 1, 1993

[54] METHOD FOR TREATING LEG WEAKNESS IN FOWL

[75] Inventor: Daniel Yam, Rishon-Lezion, Israel

[73] Assignee: Pedivet Ltd., Tel Aviv, Israel

[21] Appl. No.: 780,749

[22] Filed: Oct. 24, 1991

[30] Foreign Application Priority Data

Oct. 24, 1990 [IL] Israel .......................................... 96103

[51] Int. Cl.$^5$ .................... A61K 31/60; A61K 31/62; A61K 31/40; A61K 31/19
[52] U.S. Cl. .................................. 514/159; 514/161; 514/420; 514/568; 514/569; 514/570
[58] Field of Search ............... 514/159, 161, 568, 569, 514/570, 420

[56] References Cited

U.S. PATENT DOCUMENTS 3,147,120 9/1964 Caldwell .............................. 514/165

OTHER PUBLICATIONS

Chemical Abstracts (68:10366j) 1968.
Chemical Abstracts (87:95356d) 1977.
"Pathological defects in the Epiphyseal Cartilage of Zinc-deficient chicks", Journal of Nutrition, vol. 98, No. 1, May 1969, pp. 76–82; N. Westmoreland et al.

*Primary Examiner*—Frederick E. Waddell
*Assistant Examiner*—K. Weddington
*Attorney, Agent, or Firm*—Longacre & White

[57] ABSTRACT

A method of treating poultry suffering from leg bone joint infection and/or leg weakness by administering to the poultry an effective amount of a non-steroidal anti-inflammatory drug and composition of such drug.

10 Claims, No Drawings

METHOD FOR TREATING LEG WEAKNESS IN FOWL

BACKGROUND OF THE INVENTION a. Field of the Invention

The present invention relates to a method of treating leg weakness in poultry.

b. Description of the Prior Art

"Leg weakness" is a term used to describe a variety of abnormalities affecting locomotion in poultry. This weakness can result in an unwillingness of the birds to stand or walk and thus impair their ability to feed, which can result in starvation and even death.

Poultry farming has become an important area of agriculture and leg weakness in poultry has plagued the industry for many years and is of significant economic importance in breeding broilers, turkeys, etc. The losses due to foot and leg problems are estimated variably from 3-30%. The longer the rearing process, the greater the susceptibility of the poultry to leg weakness. This problem is particularly significant for commercial poultry breeders who operate their farms on a very tight schedule on a mass production basis. Thus the young chicks are received by the farmer and fed on a rigid schedule and with a specifically prepared feedstock which contains all the required nutrients for growth and weight gain. This process lasts, in the case of turkeys, for about 16-22 weeks, at which time the fully grown turkeys are transferred to the slaughterhouses. During this period there may be introduced into the feedstock speoifio vitamins or special nutrients or medications as the need arises, based on a monitoring of the health and growth rate of the birds. Since this process involves hundreds and even thousands of birds, any serious illness or disruption of the process with respect to individual birds affects total output, since it is difficult and at times impossible to identify and isolate, much less treat such exceptional cases.

Generally leg weakness appears in the case of turkeys after about 12 weeks. By this time the birds have grown significantly and put on substantial weight, which in some cases makes them too heavy for their legs and feet, causing inflammation and deformation thereof. Birds so affected find it difficult and painful to walk to their feeding troughs and tend to sit down, refusing to move. Apparently starvation is preferable to them than the pain and discomfort of seeking their food and drink. Once the birds have reached this stage, they lose weight and other birds attack it and eventually it dies. The farmer is not equipped to pull out these affected birds for individual treatment and thus they wind up as a loss to the overall yield of poultry product. What has happened in the industry is that the controlled breeding, feeding and management to produce higher growth rates is making the situation worse. The skeleton and the legs have to respond to the pressures of rapidly increasing weight and muscular tension.

Studies of leg weakness in poultry have shown that many nutritional deficiencies can cause these abnormalities, including several vitamin and mineral deficiencies. This however is not the case with modern poultry growing, since these nutrients are very much part of the controlled diet fed to birds. Thus B. Sauveur—Proceedings of the 7th European Poultry Congress, Paris, Volume 1:280, 1986—states that numerous studies have been devoted to the problems of leg weakness in poultry during the last 15 years without solving them. Progress has been made only in the classification of the types of leg abnormalities. Bar et al.—1987, Poult. Sci., 66:68—investigated 32 outbreaks of leg disorders in turkeys and concluded that the cause was a refractoriness to Vitamin D3. Recently Ibrahim et al. 1988. Brit. Poult. Scit., 29:721—assumed from his studies that the leg abnormalities are related to either or both mineral deposition and or collagen formation, with tannins acting either in the digestive tract or directly on the bone tissue. He was able to alleviate the problems by supplementing the feed with orthophosphoric acid or feed grade dicalcium phosphate.

SUMMARY OF THE INVENTION

We have discovered that it is possible to treat leg disease and infections in leg joints in poultry, such as chickens, ducks, geese, such as force fed geese, and specifically in turkeys, by administering to them non-steroidal anti-inflammatory inhibitors of prostaglandin synthetase and specifically prostaglandin $E_2$. Not only have we found that such treatment returns the birds to be active, walk and feed normally to gain weight, but by suitable administration of such medication during the critical period of growth, the debilitating effects of leg disease can be avoided. The administration of this medication on an industrial scale can be by introduction in the drinking water or via a slow-release formulation mixed with the food. Such slow release formulations are common for use of analgesic and other medications presently available for human consumption. We have found this medication to be effective even in terminal cases, where the turkeys have come back to function normally. Among medications we consider to be effective in treating leg disease are the analgesic and anti-inflammatory agents Diclofenac Na, NAPROXEN, IBUPROFEN, NABUMETONE, ACETYLSALICYLIC ACID, SULINDAC and INDOMETHACIN, the preferred agent being INDOMETHACIN.

DESCRIPTION OF THE PREFERRED EMBODIMENT

Non-steroidal anti-inflammatory drugs are used extensively in the management of a wide variety of musculo-skeletal disorders, including degenerative joint disease and usually without adverse effects on bone cartilage metabolism. This of course has been well established in human beings. One of these drugs, INDOMETHACIN, has analgesic, anti-inflammatory and anti-pyretic properties and has been shown to be one of the most potent inhibitors of the enzyme cyclo-oxygenase, and thus of prostaglandins synthesis. Prostaglandins, and particularly those of the E series, are known to be potent stimulators of bone resorption.

The exact dosage for use in treating the affected poultry will of course have to be determined for each medication, as well as for each species of fowl. In the case of turkeys it was found that INDOMETHACIN given via the drinking water at 2 mg. per kg. per day provided marvelous recovery of turkeys suffering from leg weakness, to the extent that they were able to complete their feeding cycle and be sent for slaughter and processing together with the rest of the group, having attained satisfactory weight gain. One of the particular advantages of using INDOMETHACIN as the medication of choice in this case is the fact that this compound is not absorbed into human tissues. Thus it is possible to stop the administration of the medication two to three days before slaughter and assure that the birds will have no residues of the medication in their body.

The following experiment was conducted with three groups of 50 turkeys each. One group was a healthy control, the second group had leg weakness without treatment and the third group had leg weakness and was treated with INDOMETHACIN at 2 mg. per kg. per day for a period of seven consecutive days administered by mouth. The following results were obtained:

|  | Mean Body Weight(Kg) | | Mean Food |
|---|---|---|---|
|  | Before | After | Consumption(Kg) |
| Healthy Control | 9.200 | 10.250 | 3.020 |
| Leg Weakness Control | 7.600 | 8.120 | 1.870 |
| Leg Weakness, IDT administered | 7.750 | 8.800 | 2.920 |

In the above example the INDOMETHACIN was administered to a whole group already suffering from leg weakness. Better results can be achieved by starting administration of the medicine as soon as leg weakness appears.

In methods and formulations similar to the recited example, regulated amounts of other preferred analgesic and anti-inflammatory agents can be administered. Such agents would preferably be selected from a group including: Diclofenac Na, NAPROXEN, IBUPROFEN, NABUMETONE, ACETYLSALICYLIC ACID and SULINDAC. The rate of and total quantity of administration would necessarily be determined according to type of and weight of the fowl. Such formulations and preferred administration processes, i.e., food or drink or both, are readily determined in view of the many existing fowl type and weight dependant vitamin and nutrient treatments already available and commonplace.

It will be understood that the non-steroidal anti-inflammatory drugs of this invention include pharmaceutically accepted derivatives of these as well.

The subjection invention has been described with respect to the best mode contemplated therefor. The subject invention is not intended to be limited in scope except by the appended claims which form a part of this specification.

What is claimed is:

1. A method of treating poultry suffering from leg bone joint infection and/or leg weakness while increasing feed utilization without incurring gizzard or intestinal ulceration comprising orally administering to the poultry a predetermined effective dosage of 2 mg/kg/day or less of a non-steroidal anti-inflammatory drug at selected intervals.

2. A method as in claim 1 wherein said drug is an inhibitor of prostaglandins synthesis.

3. A method as in claim 2 wherein said drug is an inhibitor of prostaglandins $E^2$ series.

4. A method as in claim 1, wherein said drug is selected from the group consisting of Diclofenac Sodium, NAPROXEN, IBUPROFEN, NABUMETONE, ACETYLSALICYLIC ACID, SULINDAC, or INDOMETHACIN.

5. A method as in claim 4 and applied to turkeys.

6. A method as in claim 1 wherein said drug comprises INDOMETHACIN.

7. A method as in claim 6 wherein the INDOMETHACIN is administered at 1-2 mg. per kg. per day.

8. A method as in claim 6 wherein said drug is administered through the drinking water.

9. A method as in claim 6 wherein the drug is administered via the food.

10. A method as in claim 9 wherein the drug is admininstered as a slow-release formulation.

* * * * *